United States Patent [19]

van der Maas

[11] 4,337,210
[45] Jun. 29, 1982

[54] PROCESS FOR THE PREPARATION OF COBALT (II) ACETYLACETONATE

[75] Inventor: Hendrikus J. H. van der Maas, Zuilichem, Netherlands

[73] Assignee: Chemische Fabriek Zaltbommel, Zaltbommel, Netherlands

[21] Appl. No.: 197,717

[22] Filed: Oct. 16, 1980

[30] Foreign Application Priority Data

Oct. 19, 1979 [NL] Netherlands .......................... 7907739

[51] Int. Cl.³ ............................................. C07F 15/06
[52] U.S. Cl. ................................ 260/439 R; 260/429 J
[58] Field of Search ......................... 260/439 R, 429 J

[56] References Cited

U.S. PATENT DOCUMENTS 3,474,464 10/1969 Matthews et al. .............. 260/439 R
3,946,057 3/1976 Reedy .............................. 260/439 R
4,008,260 2/1977 Kunstle ............................ 260/439 R
4,148,940 4/1979 Breininger et al. .......... 260/429 J X

OTHER PUBLICATIONS

Charles et al., J. Phys. Chem. 62, pp. 440–444, (1958).
Guter et al., J.A.C.S. 81, pp. 4686–4689, (1959).

Primary Examiner—Helen M. S. Sneed
Attorney, Agent, or Firm—Felfe & Lynch

[57] ABSTRACT

An improved process for the preparation of cobalt (II) acetylacetonate by reaction of cobalt (II) compounds with acetylacetone at elevated temperature is disclosed, wherein the reaction is carried out in an organic solvent which is immiscible with water, and forms with water an azeotropic mixture, in the vicinity of the boiling temperature of said azeotropic mixture.

10 Claims, No Drawings

PROCESS FOR THE PREPARATION OF COBALT (II) ACETYLACETONATE

BACKGROUND OF THE INVENTION

1. Field of the Invention

This invention relates to a process for the preparation of cobalt (II) acetylacetonate. In this process, a cobalt compound is reacted with acetylacetonate at elevated temperature in the presence of a specific organic solvent at a reaction temperature which does not need to exceed 100° C.

2. Discussion of Prior Art

It is known to prepare cobalt (II) acetylacetonate by reacting cobalt (II) compounds with acetylacetone. Suitable cobalt compounds are the salts of inorganic acids, such as the chloride, sulfate, nitrate, carbonate or also the hydroxide. Cobalt oxide, too, is suited for use. The reaction is carried out in an aqueous medium. Neutralization must be effected with ammonia or another weak base.

This procedure yields a product which contains two moles of water of crystallization in bound form. Elimination of the water is costly since it has to be carried out at reduced pressure (between 20 and 2 millibars) and at temperatures of up to 90° C. A further drawback of this procedure is that the dry product is highly particulate and readily disintegrates to dust.

Thus, there has been a need to provide anhydrous cobalt (II) acetylacetonate in such a way that neutralization with ammonia and the onerous washing of the crude product can be dispensed with. Moreover, there has been a need for a process yielding a product that can readily be dried to an anhydrous state.

SUMMARY OF THE INVENTION

To fill these needs, a process for the preparation of cobalt (II) acetylacetonate by reaction of cobalt (II) compounds with acetylacetone has now been developed which is characterized in that the reaction is carried out in organic solvent which is not miscible with water, and which forms an azeotropic mixture with water, in the vicinity of the boiling temperature of said azeotropic mixture. Generally speaking, the reaction is conducted at a temperature from 5° C. below the boiling point of the azeotropic mixture to 20° C. above the boiling point of the azeotropic mixture. Preferably the reaction is conducted at the boiling point of the azeotropic mixture to 20° C. above said temperature. The temperature range of 79° to 98° C. is broadly applicable, depending upon the specific solvent. A mixture of solvents can be employed.

In a preferred procedure within the new process, the azeotropic mixture of organic solvent and water forming during the reaction is continuously eliminated by distillation. The distillate can then be separated into the organic and aqueous phases, the organic phase then being recycled to the reaction mixture. This procedure, moreover, permits one to monitor the progress of the reaction by determining the amount of water distilled off. The end of the reaction is indicated by the fact that water no longer distills off an an azeotropic mixture.

However, the azeotropic mixture of solvent and water may also be distilled off discontinuously. The reaction mixture is then heated with reflux to temperatures as high as the boiling temperature of the azeotropic mixture. The reaction will proceed also before the solvent mixture is brought to ebullition, and the process in accordance with the invention can therefore generally be carried out at temperatures ranging from 60° to 100° C. With this procedure, however, it is of advantage to distill off the azeotropic mixture toward the end of the reaction.

The amount of organic solvent present in the reaction space should be at least such that the cobalt (II) acetylacetonate obtained is partly or completely dissolved therein at the reaction temperature. The amount will depend on the type of solvent chosen. Moreover, the amount should be at least such that upon cooling a readily filterable suspension of the desired salt is present in the solvent.

As soon as the reaction is terminated, the reaction mixture is allowed to cool, with the cobalt (II) acetylacetonate then precipitating. In contrast to the procedure utilizing only an aqueous medium, the process in accordance with the invention yields a precipitate that is practically free of water of crystallization. Following filtration, it can readily be dried by simple means which as such are known. Whenever possible, the product should not be heated above 90° C. as otherwise it will begin to decompose. The product is therefore preferably dried under vacuum, a pressure ranging from 20 to 100 millibars, and preferably from 30 to 60 millibars, being perfectly adequate. Higher pressures require correspondingly longer drying times.

The yields of dried end product generally range from 90 to 96 weight percent, based on the cobalt compound used. Thus they are substantially higher than obtained by prior art processes, which give yields between 60 and 75 percent.

Suitable for use as solvents in accordance with the invention are both aromatic and aliphatic or cycloaliphatic solvents. The only requirement is that they be practically immiscible with water and form with water an azeotropic mixture whose boiling point is below 100° C. Examples of aromatic hydrocarbons which satisfy these requirements are benzene, anisole, the xylenes, and chlorobenzene. Suitable aliphatic solvents include aliphatic saturated hydrocarbons, chlorinated hydrocarbons, ketones and alkyl esters of lower carboxylic acids. Examples are: Hexane, heptane, nonane, cyclohexane, dichloroethane, trichloroethane, cyclohexanone, cyclopentanone, the methyl to butyl esters of $C_1$ to $C_4$ carboxylic acids, such as formic acid butyl ester, acetic acid propyl ester, propionic acid ethyl ester and allyl acetate. The preferred solvents are benzene and n-heptane.

The preferred cobalt compound is cobalt (II) hydroxide. However, the reaction may also be carried out with basic cobalt (II) carbonate or any of the cobalt salts mentioned above or cobalt oxide.

The reactants are generally reacted in stoichiometric ratios since the yields of the process in accordance with the invention are nearly quantitative. However, acetyl acetone is best used in a slight excess of up to 10 percent of the stoichiometrically required amount. After the cobalt (II) acetylacetonate has been filtered off, this excess can be recycled to a new batch along with the recovered mother liquor. It is not necessary to work up the mother liquor.

Cobalt (II) acetylacetonate finds use as a catalyst in polymerization or copolymerization, as of methacrylic acid esters or of butadiene to stereospecific products, and as a catalyst in liquid-phase oxidation or in hydrogenation. It is also used as a coating for glass surfaces and as an antioxidant in lubricants.

EXAMPLE 1

4600 ml n-heptane was introduced into a reaction vessel equipped with a distilling apparatus, and 1068.1 g (11.5 moles) cobalt hydroxide was then suspended therein. This mixture was heated to a temperature of 90° to 94° C., with some reflux occurring. 2417.5 g acetylacetone was then added to this mixture over a period of 4 hours, during which time the temperature of the reaction vessel was maintained at 90° to 94° C. Refluxing increased in the course of the reaction. The azeotrope distilling over was collected and the water was separated by means of a separating funnel while the supernatant heptane was recycled to the reaction mixture.

In this way, 405 ml water was separated over a period of 8 hours. This corresponds to 98% of the theoretically separable amount of 414 ml.

The reaction mixture was then cooled to 15° C. This resulted in the precipitation of cobalt (II) acetylacetonate crystals of a dark-violet color. These were separated by filtration and washed with a total of 1000 ml heptane. The solvent was then drawn off by suction.

After the product obtained in this manner had been dried in an oven at a temperature of 40° C. and a pressure of 40 millibars, a total of 2856.8 g of the desired cobalt (II) acetylacetonate was obtained. This corresponds to a yield of 96.6%. The cobalt content was between 22.6 and 22.7%, and the water content under 1%.

EXAMPLE 2

The mother liquor from Example 1 and sufficient wash heptane from that example to bring the total amount of liquid to 4600 ml were introduced into the reaction vessel of Example 1, to which 1068.8 g cobalt hydroxide was likewise fed. The procedure then followed was the same as that described in Example 1.

A total of 2862.4 g cobalt (II) acetylacetonate was obtained, which corresponds to a yield of 96.7%. The cobalt content was between 22.6 and 22.7%, and the water content was under 0.5%.

EXAMPLE 3

In an apparatus corresponding to that of Example 1, 128 g basic cobalt carbonate was stirred into 500 ml n-heptane. A total of 212 g acetylacetone was then added with stirring. The evolution of gas was observed at once, and the internal temperature rose to 45° C. A change in the color and crystal shape of the solid product was also discernible.

The reaction mixture was then maintained for 5 hours at boiling temperature, a total of 54 ml water being collected from the azeotropic mixture distilling over. During that time, the cobalt acetylacetonate, initially pink, took on a deep violet coloration.

The reaction mixture was then cooled to 15° C., and the solid was separated by filtration and washed with 75 ml heptane. After drying, 253.1 g cobalt (II) acetylacetonate with a metal content between 22.9 and 23.0% and a water content of not more than 0.5% was obtained. The yield thus was 98.5%.

EXAMPLE 4

128 g basic cobalt carbonate was suspended in the mother liquor and wash water of Example 3. The total amount of solvent was 550 ml. 212 g acetylacetone was then added to this suspension with stirring, during which the internal temperature rose to 43° C. and a pronounced evolution of gas was observed.

The reaction mixture was then maintained for 6 hours at boiling temperature, a total of 53.6 ml water in the form of the azeotrope with heptane distilling over.

The further procedure was the same as in Example 3. A total of 254.3 g cobalt (II) acetylacetonate with a metal content between 22.8 and 22.9% was obtained. The water content was less than 0.5%.

What is claimed is:

1. In a process for the preparation of cobalt (II) acetylacetonate by contacting a cobalt (II) compound with acetylacetone at an elevated temperature, the improvement wherein the reaction is carried out in an organic solvent which is immiscible with water, and forms with water an azeotropic mixture, in the vicinity of the boiling temperature of said azeotropic mixture.

2. A process according to claim 1, wherein an organic solvent is used which in azeotropic mixture with water boils at temperatures of up to 100° C.

3. A process according to claim 1, wherein the azeotropic mixture of solvent and water produced in the reaction is distilled off as it is produced.

4. A process according to claim 1, wherein said cobalt (II) compound is cobalt (II) hydroxide.

5. A process according to claim 1, wherein said cobalt (II) compound is basic cobalt (II) carbonate.

6. A process according to claim 1, wherein said solvent is an aromatic, aliphatic or cycloaliphatic solvent.

7. A process according to claim 6, wherein said solvent is selected from the group consisting of benzene, anisole, xylenes, chlorobenzene, hexane, heptane, nonane, cyclohexane, dichloroethane, trichloroethane, cyclohexanone, cyclopentanone and the methyl to butyl esters of $C_1$ to $C_4$ carboxylic acid.

8. A process according to claim 1, wherein the solvent is an aliphatic saturated hydrocarbon, chlorinated hydrocarbon, ketone or an alkyl ester of a lower carboxylic acid.

9. A process according to claim 1, wherein the solvent is benzene, n-heptane or a mixture thereof.

10. A process according to claim 1, wherein the process is carried out at a temperature from 60° to 100° C. and the azeotropic mixture of solvent and water is distilled off toward the end of the reaction.

* * * * *